United States Patent [19]

Levy et al.

[11] Patent Number: 4,883,790

[45] Date of Patent: Nov. 28, 1989

[54] WAVELENGTH-SPECIFIC CYTOTOXIC AGENTS

[75] Inventors: Julia G. Levy; David Dolphin, both of Vancouver; Jack K. Chow, Burnaby, all of Canada

[73] Assignee: University of British Columbia, Vancouver, Canada

[21] Appl. No.: 41,680

[22] Filed: Apr. 23, 1987

Related U.S. Application Data

[63] Continuation-in-part of Ser. No. 5,204, Jan. 20, 1987.

[51] Int. Cl.$^4$ ............................................. A61K 31/66
[52] U.S. Cl. .................................................... 540/145
[58] Field of Search ......................... 540/145; 514/410

[56] References Cited

U.S. PATENT DOCUMENTS

| | | | |
|---|---|---|---|
| 2,951,800 | 9/1960 | Sharp | 540/145 X |
| 4,649,151 | 3/1987 | Dougherty et al. | 540/410 |
| 4,675,338 | 6/1987 | Bommer et al. | 514/410 |

OTHER PUBLICATIONS

Morgan et al., J. Chem. Soc., Chem. Commun., 1984, pp. 1047–1048.
Richter et al.–JNCI, vol. 79, No. 9, 12-1983, pp. 1327–1332.
Pangka et al., J. Organic Chem., 51:1094, 1986.

*Primary Examiner*—Leonard Schenkman
*Attorney, Agent, or Firm*—Irell & Manella

[57] ABSTRACT

A group of hydro-monobenzoporphyrins "green porphyrins" (Gp) having absorption maxima in the range of 670–720 nanometers is useful in treating disorders which are subject to hematoporphyrin derivative (HPD) treatment in the presence of light. The use of the Gp of the invention permits the irradiation to comprise wavelengths other than those absorbed by blood. The Gp of the invention may also be conjugated to receptor ligands or to specific immunoglobulins or fragments thereof to target specific tissues or cells for the radiation treatment. Use of these materials permits lower levels of drug to be used, thus preventing side reactions which might destroy normal tissues.

11 Claims, 1 Drawing Sheet

WAVELENGTH-SPECIFIC CYTOTOXIC AGENTS

CROSS-REFERENCE TO RELATED PATENT APPLICATION

This is a continuation-in-part of U.S. Ser. No. 005,204, filed 20 January 1987.

FIELD OF THE INVENTION

The invention relates to the use of light absorbing compounds to mediate the destruction of unwanted cells or tissues by irradiation. Specifically, the invention relates to the use of hydro-monobenzo porphyrin derivatives having absorption maxima in the range 670–720 nanometers to mediate the irradiation of cells or tissues to be destroyed, and to the use of these compounds conjugated to receptor ligands or to immunoglobulins or their immunospecific fragments to focus the effects of the irradiation on particular target tissues.

BACKGROUND OF THE INVENTION

The use of hematoporphyrin and its acetylated derivative mixture hematoporphyrin derivative (HPD) systemically, combined with irradiation, for the detection and treatment of malignant cells has, by this time, some considerable history. HPD is a mixture of hematoporphyrins including hematoporphyrin itself, hydroxyethyl vinyl deuteroporphyrin, protoporphyrin, and dihematoporphyrin ether. (See, e.g., "Porphyrin Photosensitization", Kessee, D., et al, eds. (1983) Plenum Press.) HPD seems "naturally" capable of localizing in malignant cells. When irradiated, it has two properties which make it useful. First, when irradiated with ultraviolet or visible light, it is capable of fluorescence, and thus is useful in diagnostic methods related to detection of malignancy (see, for example, Kessee, et al. (supra); Gregory, H. B. Jr., et al, *Ann Surg* (1968) 167:827–829). More pertinent to the present invention is the capacity of HPD, when irradiated with visible light, to exhibit a cytotoxic effect on the cells in which it is localized (see, for example, Diamond, I., et al, *Lancet* (1972) 2:1175–1177; Dougherty, T. J., et al, *Cancer Research* (1978) 38:2628–2635; Dougherty, T. J., et al, "The Science of Photo Medicine" (1982) J. D. Regan & J. A. Parrish eds., pp. 625–638; Dougherty, T. J., et al, "Cancer: Principles and Practice of Oncology" (1982) V. T. DeVita Jr., et al, eds., pp. 1836–1844). Although it has not been definitively established, the effect of HPD in killing cells seems to be due to the formation of singlet oxygen upon irradiation (Weishaupt, K. R., et al, *Cancer Research* (1976) 36:2326–2329). Several mechanisms for this effect have been proposed, and it has recently been shown that the active ingredient in HPD which mediates the cytotoxic effect of visible light irradiation is dihematoporphyrin ether (DHE) (Dougherty, T. J., et al, "Porphyrin Localization and Treatment of Tumors" (1984) pp. 301–314; Dougherty, T. J., *CRC Critical Reviews in Oncology/Hematology* (1984) 2:83–116).

While the treatment of tumors with HPD relies on the intrinsic ability of HPD to localize in malignant cells, a considerable improvement and refinement in specificity has been achieved by conjugating hematoporphyrin itself to tumor-specific antibodies. For example, when hematoporphyrin was coupled to monoclonal antibodies directed to a murine myosarcoma cell line M1, administration of anti-M1 hematoporphy-rin-conjugates to tumor-bearing animals followed by exposure to incandescent light resulted in the suppression of M1 growth (Mew, D., et al, *J Immunol* (1983) 130:1473–1477). In additional work, hematoporphyrin was conjugated to a monoclonal antibody specific to an antigen associated with a human leukemia (CAMAL) and the conjugates were shown to mediate the irradiation-induced killing of leukemic cells specifically, in vitro (Mew, D., et al, *Cancer Research* (1985) 45:4380–4386).

While the conjugation of hematoporphyrin to immunoglobulins specific for targeted cells refines the ability of the hematoporphyrin to home to the desired cells or tissue, this still dose not solve another problem ancillary to this general therapeutic approach, namely that the wavelength for irradiation required to activate the hematoporphyrin or HPD, which is in the range of 630 nanometers, is also an energy which is readily absorbed by the porphyrins and other natural chromophores in the blood and other tissues. Therefore, relatively large amounts of the hematoporphyrin or HPD must be administered, often resulting in oversensitization of the patient to light in general. It would be desirable to administer compounds to mediate the effects of irradiation in a lower amount, thus avoiding the problems of hypersensitivity exhibited nonspecifically throughout the subject organism.

DISCLOSURE OF THE INVENTION

The invention provides light absorbing compounds capable of exhibiting light mediated cytotoxic effects. These compounds may be administered in relatively low dosage due to their capability to absorb radiation whose energy range is outside of that normally absorbed by the components present in high concentration in the blood or other tissues, in particular the porphyrin residues normally associated with hemoglobin and myoglobin. Therefore, by providing these modified porphyrins at lower concentration, the irradiation treatment can be conducted at a wavelength at which the native chromophores do not compete for photons with the active compounds. This results in greater depth of penetration of the light and reduces hypersensitivity of nontarget tissues. These active compounds are modified porphyrins which, by virtue of their derivatization, undergo a shift in absorption maxima so that they appear grean rather than red, indicating their absorption of wavelengths in the red-orange range. This collection of derivatives has therefore been nicknamed "green porphyrin" and has been shown to confer sensitivity on target cells at concentrations greater than 10-fold lower than those required for hematoporphyrin or HPD.

In addition, the modified porphyrins (referred to as "green porphyrin" or "Gp" herein) of the invention can be conjugated to receptor ligands or to immunoglobulins or immunospecific portions of immunoglobulins permitting them to be specifically concentrated in a desired target tissue. This conjugation permits further lowering of the required does levels since the material is not wasted in distribution into tissues whose destruction, far from being desired, is needed to be maintained.

Thus, in one aspect, the invention relates to conjugates of the formulas Re*-L-Gp and Ig-L-Gp wherein Re* represents a receptor ligand capable of binding a receptor at a cell surface, Ig represents an immunoglobulin or an immunologically reactive portion thereof, Gp represents a hydro-monobenzoporphyrin derivative having an absorption maximum in the range of 670–720 nanometers, and L represents either a covalent bond linking these components or a linking moiety covalently linked to each of the Re* or Ig and Gp. Preferably, the Gp is selected from a group of porphyrin derivatives obtained using Diels-Alder reactions with porphyrin nuclei under conditions which effect a reaction at only one of the two available conjugated, nonaromatic diene structures present in the protoporphyrin-IX nucleus.

In other aspects, the invention relates to methods of effecting cytotoxicity against target cells using the hydro-monobenzoporphyrins in the presence of red light either alone or as the conjugates described above. In other aspects, the invention relates to pharmaceutical compositions containing these active ingredients.

MODES OF CARRYING OUT THE INVENTION

The Hydro-monobenzoporphyrins

Figure 1:
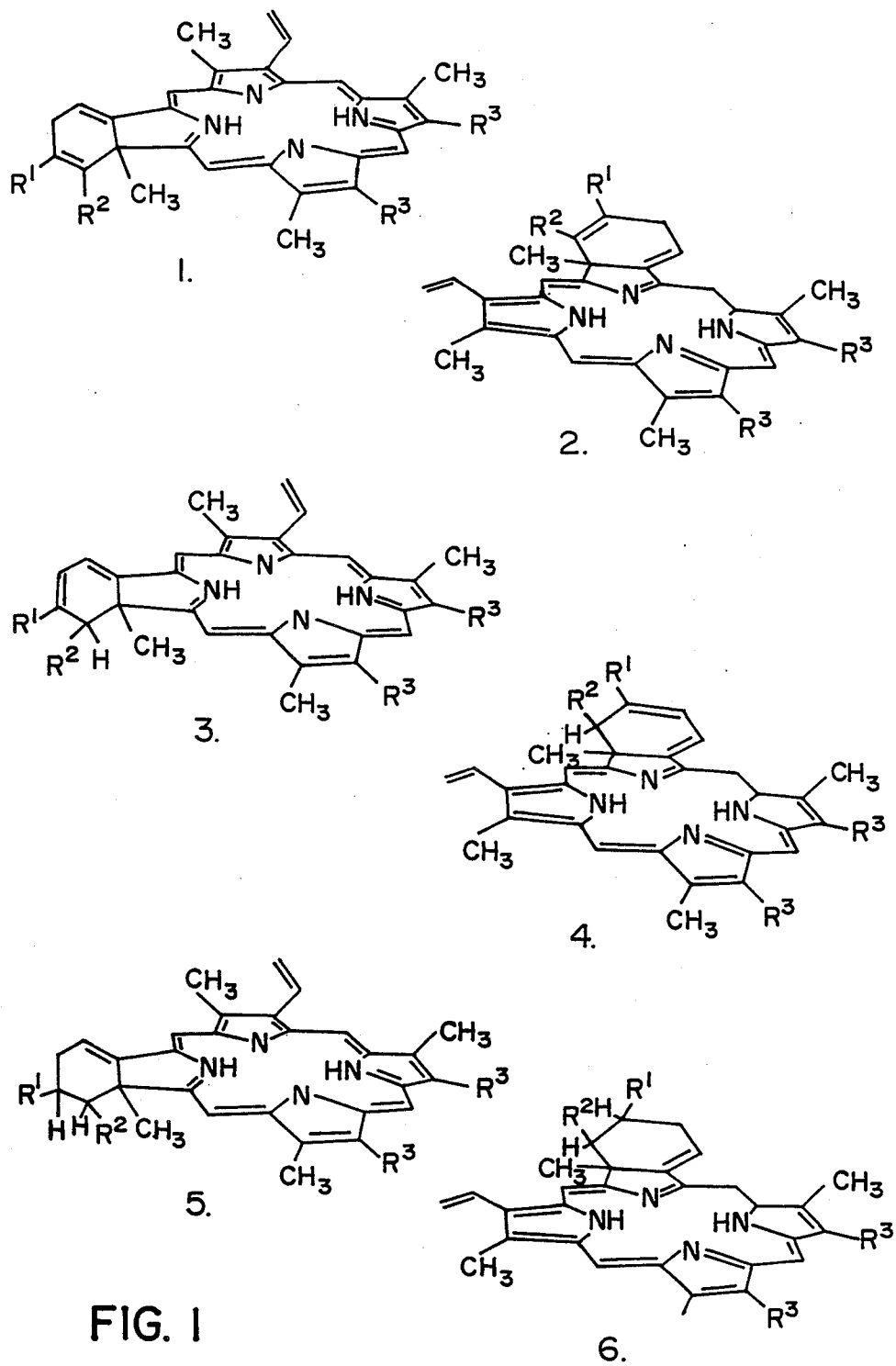
FIG. 1 shows the structures of the green porphyrin compounds used in the method and conjugates of the invention.

All of the compositions of the invention employ as the light absorbing compound, a derivative of a porphyrin nucleus which has a light absorption maximum in the range of 670–720 nanometers. In general, this shift is achieved by effectively saturating one of the two $\pi$-bonds in one, but not two, of the four pyrrole rings which constitute the typical porphyrin nucleus. In protoporphyrin-IX, for example, two of the pyrroles contain vinyl substitutions such that the exocyclic $\pi$-bond is conjugated to one of the two $\pi$-bonds in the ring. A Diels-Alder reaction involving this conjugated system results in shifting the pyrrole $\pi$-bond outside the ring and results in the desired shift in absorption maximum.

Specific preparation of compounds useful in the invention is described by Morgan, A. R., et al, *J Chem Soc Chem Commun* (1984) pp. 1047–1048; and by Pangka, B. S., et al, *J Organic Chem* (1986) 51:1094. As described in these publications, protoporphyrin-IX dimethyl ester, when reacted with strong Diels-Alder dienophile reagents such as tetracyanoethylene, is derivatized to the hydro-dibenzo derivatives. However, when more weakly electron withdrawing groups are utilized on the Diels-Alder reagent, hydro-monobenzo derivatives are formed. Thus, there are obtained compounds shown as formulas 1 and 2 of FIG. 1 wherein $R^1$ and $R^2$ represent the original Diels-Alder reagent substituents and $R^3$ represents the substituents natively or originally on the porphyrin nucleus.

$R^1$ and $R^2$ are ordinarily carboxy or carbalkoxy groups but may also be derivatives of sulfonic acid such as the alkylsulfonic esters, or may be sulfone derivatives, optionally substituted phenyl groups, or other electron-withdrawing substituents. As used herein, carboxy is conventionally defined as —COOH, carbalkoxy is —COOR wherein alkyl is a saturated hydrocardon of 1–6 carbon atoms such as methyl, n-hexyl, 2-methylpentyl, t-butyl, n-propyl, and so forth. Sulfonic esters have the formula SO$_3$R wherein R is alkyl is above-defined, or is aryl, wherein aryl is phenyl optionally substituted with 1–3 substituents independently selected from halo (fluoro, chloro, bromo or iodo), lower alkyl (1–4C) or lower alkoxy (1–4C). In addition, $R^3$ can itself be aryl—i.e., phenyl optionally substituted as above defined.

$R^3$ in protoporphyrin-IX is 2-carboxyethyl (—CH$_2$CH$_2$COOH). However, the nature of $R^3$, unless it contains a $\pi$-bond conjugated to ring $\pi$-bond, is ordinarily not relevant to the progress of a Diels-Alder reaction or to the effectiveness of the resulting product, and $R^3$ can thus be, for example, lower alkyl (1–4C), or $\omega$-carboxyalkyl (2–6C). The carboxy groups may also be in the form of the esters (1–6C) or amides (1–10C). The $R^3$ substituent may also be substituted with halogen as above-defined, or with other nonreactive substituents.

The hydro-monobenzoporphyrins which result from the Diels-Alder reaction described in the cited references can also be isomerized as therein described (see Pangka et al. (supra) to compounds of formulas shown as 3 and 4 of FIG. 1 by treatment with suitable reagents such as triethylamine in methylene chloride or 1,5-diaza bicyclo[5.4.0] undec-5-ene (DBU). The stereochemistry of the product is determined by the choice of reagent. In addition, the Diels-Alder products can be selectively reduced by treating with hydrogen in the presence of palladium on charcoal to give the saturated ring analogs, shown as formulas 5 and 6 in FIG. 1, corresponding to the respective Diels-Alder products.

It will be noted that all of the compounds of FIG. 1 contain at least 1 chiral center and therefore exist as optical isomers. The conjugates and methods of the invention include compounds having both configurations of the chiral carbons, whether the compounds are supplied as isolates of a single stereoisomer or are mixtures of enantiomers and/or diasteriomers. Separation of mixtures of diasteriomers may be effected by any conventional means; mixtures of enantiomers may be separated by usual techniques of reacting them with optically active preparations and separating the resulting diasteriomers.

The name dihydro-monobenzoporphyrin describes the Diels-Alder direct and rearrangement products; tetrahydro-monobenzoporphyrin describes the foregoing reduced products, and hexahydro-monobenzoporphyrin describes the analogs containing the exocyclic "benzo" ring completely reduced. Hydro-monobenzoporphyrin is used generically to include all three classes of oxidation state. The monobenzoporphyrins per se are outside the scope of the invention as their absorption maxima do not fall within the required range.

THE TARGET CELL-SPECIFIC COMPONENT

The target cell-specific component can be an immunoglobulin or portion thereof or a receptor ligand. The immunoglobulin component can be any of a variety of materials. It may be derived from polyclonal or monoclonal antibody preparations and may contain whole antibodies or immunologically reactive fragments of these antibodies such as F(ab')$_2$, Fab, or Fab' fragments. Use of such immunologically reactive fragments as substitutes for whole antibodies is well known in the art. See, for example, Spiegelberg, H. L., in "Immunoassays in the Clinical Laboratory" (1978) 3:1–23.

Polyclonal anti-sera are prepared in conventional ways by injecting a suitable mammal with antigen to which antibody is desired, assaying the antibody level in serum against the antigen, and preparing anti-sera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, H. L, supra.

Particularly useful antibodies exemplified herein include the monoclonal antibody preparation CAMAL-1 which can be prepared as described by Malcolm, A., et al, *Ex Hematol* (1984) 12:539–547; polyclonal or monoclonal preparations of anti-M1 antibody as described by Mew, D., et al, *J Immunol* (1983) 130:1473–1477 (supra) and B16G antibody which is prepared as described by Maier, T., et al, *J Immunol* (1983) 131:1843; Steele, J. K., et al, *Cell Immunol* (1984) 90:303.

The foregoing list is exemplary and certainly not limiting; once the target tissue is known, antibody specific for this tissue may be prepared by conventional means. Therefore the invention is applicable to effecting toxicity against any desired target.

The receptor ligand refers to a moiety which finds a receptor at cell surfaces, and thus retains contours and charge patterns which are complementary to those of the receptor. The receptor ligand is symbolized in the formulas of the compounds of the invention as Re*, wherein the asterisk indicates that the moiety bound in the compound of the invention is not the receptor itself, but a substance complementary to it. It is well understood that a wide variety of cell types have specific receptors designed to bind hormones, growth factors, or neurotransmitters. However, while these specific embodiments of receptor ligands are known and understood, the term "receptor ligand", as used herein, refers to any substance, natural or synthetic, which binds specifically to the receptor.

Examples of such receptor ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmitters, such as acetylcholine, serotonin, and dopamine. Any analog of these substances which succeeds in binding to the receptor is also included.

LINKAGE

The conjugation of the target-cell-specific component to the hydro-monobenzoporphyrin can be effected by any convenient means. For proteins, such as Ig and certain Re*, a direct covalent bond between these moieties may be effected, for example, using a dehydrating agent such as a carbodiimide, in which case L represents a covalent bond. A particularly preferred method of covalently binding hydro-monobenzoporphyrins to the immunoglobulin moiety is treatment with 1-ethyl-3-(3-dimethylamino propyl) carbodiimide (EDCI) in the presence of a reaction medium consisting essentially of dimethyl sulfoxide (DMSO). A preparation using this preferred procedure is illustrated in Example 3 below.

Of course, other dehydrating agents such as dicyclohexylcarbodiimide or diethylcarbodiimide could also be used as well as conventional aqueous and partially aqueous media.

Nonprotein receptor ligands can be conjugated to the Gp according to their relevant functional groups by means known in the art.

The active moieties of the conjugate may also be conjugated through linker compounds which are bifunctional, and are capable of covalently binding each of the two active components. A large variety of these linkers is commercially available, and a typical list would include those found, for example, in the catalog of the Pierce Chemical Co. These linkers are either homo- or heterobifunctional moieties and include functionalities capable of forming disulfides, amides, hydrazones, and a wide variety of other linkages.

Other linkers include polymers such as polyamines, polyethers, polyamine alcohols, derivatized to the components by means of ketones, acids, aldehydes, isocyanates, or a variety of other groups.

The techniques employed in conjugating the active moieties of the conjugate include any standard means and the method for conjugation does not form part of the invention. Therefore, any effective technique known in the art to produce such conjugates falls within the scope of the invention, and the linker moiety is accordingly broadly defined only as being either a covalent bond or any linker moiety available in the art or derivable therefrom using standard techniques.

ADMINISTRATION AND USE

The conjugates of the invention, or the hydromonobenzoporphyrins when employed alone are formulated into pharmaceutical compositions for administration to the subject using techniques known in the art generally. A summary of such pharmaceutical compositions may be found, for example, in *Remington's Pharmaceutical Sciences*, Mack Publishing Co., Easton, Pennsylvania, latest edition.

The conjugates and hydro-monobenzoporphyrins of the present invention would normally be administered systemically, in particular by injection. Injection may be intravenous, subcutaneous, intramuscular, or, even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in *Remington's Pharmaceutical Sciences* (supra).

If the treatment is to be localized, such as for the treatment of superficial tumors or skin disorders, the active conjugates or hydro-monobenzoporphyrins may be topically administered using standard topical compositions involving lotions, suspensions, or pastes.

The quantity of conjugate or green porphyrin derivative to be administered depends on the choice of active ingredient, the condition to be treated, the mode of administration, the individual subject, and the judgment of the practitioner. Depending on the specificity of the preparation, smaller or larger doses may be needed. For compositions which are highly specific to target tissue, such as those which comprise conjugates of the green porphyrin with a highly specific monoclonal immunoglobulin preparation or specific receptor ligand, dosages in the range of 0.05–1 mg/kg are suggested. For compositions which are less specific to the target tissue, larger doses, up to 1–10 mg/kg may be needed. The foregoing ranges are merely suggestive, as the number of variables in regard to an individual treatment regime is large and considerable excursions from these recommended values are expected.

EXAMPLES

The following examples are intended to illustrate the invention but not to limit its scope.

EXAMPLE 1

In Vitro Toxicity of Green Porphyrins

Cells were washed three times in serum-free medium (DME), counted and made up to a concentration of $10^7$ cells per ml.

For the "affinity" assay, in the dark, 100 μl of the cell suspension and 100 μl of the test or control compound were mixed. "Labeling" was allowed to continue for one hour at 4° C., and labeled cells were washed in the dark three times with 3 ml medium each time and resuspended in fresh medium. The resuspended cells were then subjected to light exposure at 300-750 nanometers for 30 minutes.

In a "direct" assay the cells were irradiated immediately upon addition of the test or control compound.

The effect of irradiation was estimated using methods appropriate to the target cells.

When human erythrocytes (RBCs) were used as test cells, the hemolysis caused by irradiation of control (hematoporphyrin, Hp) labeled and green porphyrin (formula 1) labeled cells were estimated visually. Repeated tests showed the green porphyrin to be 20-30 times more active than Hp in this assay. Thus, a concentration of 250 ng/ml Hp was required under the above conditions to obtain 50% hemolysis while only 10 ng/ml of green porphyrin was required to hemolyze 50% of the RBCs.

When the murine mastocytoma cell line P815 was used, the results were determined as follows:

The cells were labeled as above using concentrations of 10-50 ng/ml of Hp as control and the green porphyrin of formula 1 as the test substance. The resuspended cells were treated with 300-750 nm light for 30 minutes and the viability resulting was estimated by direct counting using eosin-Y exclusion, a standard procedure for differentiating living from dead cells.

In other determinations conducted as above, the cells recovered from light exposure were assayed for viability by incubating them for 18 hours in 10 μCi/ml tritium-labeled thymidine according to the standard procedure whereby thymidine incorporation is equated with viability. The cells were harvested and radioactivity uptake was measured by a scintillation counter.

Fifty percent of the P815 cells were killed at 580 ng/ml Hp, but at only 32 ng/ml green porphyrin.

The results of each determination on a variety of cells is shown in Table 1 ($LD_{50}$ is the concentration of compound required to kill 50% of the cell population).

TABLE 1

| Cell line | $LD_{50}$ (ng/ml) | | | |
| --- | --- | --- | --- | --- |
| | Direct test | | Affinity test | |
| | Gp | Hp | Gp | Hp |
| Normal lymphocytes | 4.2 | 31 | 11 | 100 |
| HL-60 | 3.5 | 64 | 7.2 | 145 |
| K562 | 70 | 770 | 33 | 2.500 |
| KG-1 | 163 | 960 | 80 | 2.350 |
| P815 | 32 | 580 | 26 | 1.300 |

EXAMPLE 2

Selective Binding of Green Porphyrin

P815 cells were incubated as described in Example 1 using 1-200 ng/ml Hp or green porphyrin of Formula 1. The cells were labeled in the dark for 30 minutes, washed free of unadsorbed porphyrins, resuspended, and then exposed to 300-750 nm light for another 30 minutes. Viability of the cells was established by tritiated thymidine incorporation after labeling with 20 μCi/ml tritiated thymidine and incubating at 37° C. for 18 hours.

The results showed that 50% of the P815 cells were destroyed at 6-20 ng/ml green protoporphyrin or at 200 ng/ml hematoporphyrin.

EXAMPLE 3

Preparation of Immunoconjugates

This example describes methods of preparation for immunoconjugates of four different antibody preparations with either hematoporphyrin (Hp) or the green porphyrin (Gp), in this example, that of Formula 1. The antibodies employed were CAMAL-1, anti-M1 antibody, and B16G antibody, all prepared as described hereinabove, and affinity purified rabbit/anti-mouse Ig (RαMIg). In addition, a purified irrelevant monoclonal preparation (C-MAb) was used where a control was desired.

One preparation of the conjugates is basically as described in Mew, D., et al, *J Immunol* (1983) 130:1473 (supra). Briefly, to 220 mg Hp.0.2 HCl (Sigma Chemical Co., St. Louis, MO) in 25 ml water and 0.8 ml N,N-dimethylformamide was added 20 mg 1-ethyl-3-(3-dimethylaminopropyl)-carbodiimide HCl (EDCI) in 0.6 ml water. After 30 minutes, this solution was mixed with 15 mg of the antibody protein dissolved in 5 ml distilled water and incubated for 5 hours. During this period, the pH of the solution was monitored and adjusted to between 6 and 7. Then 50 μl of monoethanolamine were added, and the solution was allowed to stand overnight at room temperature. The solution was dialyzed against 0.001 M phosphate buffer pH 7.4 for four days with three changes per day and overnight against PBS. The conjugate of green porphyrin is analogously prepared.

In a preferred method, the conjugation is conducted in an entirely nonaqueous solvent.

In a typical protocol, 2 ml of a dispersion in DMSO containing 5 mg each of the Hp or Gp and the dehydrating agent is prepared and stirred for 30 minutes at room temperature under nitrogen. To this is added a dispersion containing 2 mg of the appropriate immunoglobulin in 2 ml of DMSO, and the resulting mixture stirred for another 10 minutes. This mixture is then worked up by dilution in phosphate-buffered saline, pH 7.4 (PBS) by adding 5 times the volume of PBS containing 50 μl monoethanolamine, and is then dialyzed against PBS using three changes of wash.

Alternatively, 2 ml of a dispersion containing 5 mg each of Hp or Gp, a linking agent, and a dehydrating agent is prepared and stirred for approximately 15 minutes at room temperature under nitrogen. To this is then added a dispersion containing about 2 mg of the immunospecific protein in 2 ml of tetrahydrofuran and the resulting mixture stirred for another 10 minutes. The mixture is then worked up as described above.

The foregoing procedures are appropriate for CAMAL-1 and for the remaining antibody preparations above listed.

In addition, the following preparations were made specifically with B16G and RαMIg:

B16G 11 mg of hematoporphyrin plus 11 mg EDCI in 4 ml spectral grade DMSO was stirred for 30 minutes under nitrogen at room temperature before the addition of 20 mg lyophilized B16G antibodies, prepared as described by Maier, T., et al, *J Immunol* (1983) 131:1843, in 2 ml DMSO. The resulting mixture was stirred for 40 seconds at room temperature and worked up as described above. The resulting product contained 375 μg Hp/mg B16G. A similar procedure is used substituting Gp for Hp.

RαMIg

400 μg of EDCI and 400 μg hematoporphyrin in 1 ml DMSO were stirred for 30 minutes under nitrogen at room temperature as above before the addition of 800 μg lyophilized RαMIg antibodies, prepared as described by Mew, D., et al, *J Immunol* (1983) 1473–1477, in 1 ml DMSO. The resulting mixture was stirred for 30 seconds and worked up as described above to obtain a product containing 200 μg Hp/mg RαMIg. A similar procedure is used substituting Gp for Hp.

EXAMPLE 4

Specificity of Immunoconjugates in Vitro

In the following determinations, the levels of antibody labeling were as follows, expressed as μg Hp or green porphyrin (Gp) per mg immunoglobulin:
RαMIg-Hp: 110 μg/mg;
B16G-Hp, 156 μg/mg;
CAMAL-1-Hp, 260 μg/mg;
Anti-M1-Hp, 170 μg/mg;
C-MAb-Hp, 95 μg/mg;
RαMIg-Gp, 120 μg/mg;
B16G-Gp, 165 μg/mg;
CAMAL-1-Gp, 75 μg/mg;
C-MAb-Gp 90 μg/mg.

The Ig-Hp and Ig-Gp conjugates are tested against cells in vitro by mixing the conjugates with the appropriate cell types, along with suitable controls, and then exposing the labeled cells to irradiation. Procedures for carrying out this assay were described in detail in Mew, D., et al, *Cancer Research* (1985) for CAMAL-1, and by Mew, D., et al, *J Immunol* (1983) for Anti-M1, both references cited hereinabove and incorporated herein by reference.

Briefly, for CAMAL-1, three cell lines, WC4, WC6 and WC2 (WC4 and WC6 produces the CAMAL antigen, but WC2 does not), are labeled with the appropriate Ig-Hp or Ig-Gp preparation as described above in Example 1. The labeled cell preparations containing $10^6$ cells each are introduced to Rose chambers and exposed to light activation with a laser at 630 nm. The results for various preparations are then compiled.

For the anti-M1 conjugate, M1 tumor cells are used as target cells and treated with the Ig-Hp, Ig-Gp conjugates or drug or antibody alone or the combination of antibody and drug, but uncoupled, by incubating them in 6% $CO_2$ humidified incubator at 37° for two hours. The cells are washed three times in PBS and then plated and exposed to fluorescent light overnight. The cells are assessed for viability by tritiated thymidine uptake as above.

For the B16G conjugates, A10, P815, and L1210 cells are used as target cells. (A10 cells are a T-cell hybridoma which secretes a B16G-reactive T suppressor factor; P815 cells are also reactive with B16G.) The in vitro study is done using a direct method employing the B16G-Hp or B16G-Gp conjugate or indirectly using unlabeled B16G antibodies and labeled RαMIg-Hp or RαMIg-Gp.

In a direct method, $5 \times 10^5$ cells are suspended in 1 ml DME/Hepes containing the appropriate Ig-drug conjugate as test or control at Hp or Gp concentrations of 320, 160, 80, 40 and 20 ng drug/ml. The cells are incubated in the dark at 37° for one hour, then washed three times in 5 ml DME/Hepes and then resuspended in 1 ml of the same buffer. Three 100 μl test portions of the labeled preparations are dispensed into flat bottom microtiter wells and the remainder of the cell suspensions (700 μl) are exposed to incandescent light (22.5 mW/cm$^2$) at a distance of 20 cm for one hour. Then three additional 100 μl aliquots are removed to microtiter wells. Tritium-labeled thymidine diluted in DME/Hepes containing 20% FCS is then added to all microtiter wells in 100 μl aliquots so that 2 μCi of labeled thymidine is added to each well. Cultures are incubated for 18 hours at 37° C. and humidified 10% $CO_2$ and then harvested on a MASH harvester. Thymidine incorporation was measured with an Hp scintillation counter (Tri-Carb Model 4550). The results of this study for Ig-Hp are shown in Table 2.

TABLE 2

| B16G Hp | % killing of cell lines | | |
|---|---|---|---|
| (ng Hp/ml) | A10 | P815 | L1210 |
| 320 | 100 | 70 | 55 |
| 160 | 100 | 50 | 10 |
| 80 | 100 | 20 | 0 |
| 40 | 65 | 10 | 0 |
| 20 | 20 | 0 | 0 |
| C—MAb-HP | | | |
| 320 | 63 | 75 | 50 |
| 160 | 35 | 48 | 15 |
| 80 | 0 | 25 | 0 |
| 40 | 0 | 12 | 0 |
| 20 | 0 | 0 | 0 |

In an indirect assay, the A10 suspended cells, prepared as described above, are exposed to 50 μg/ml of either B16G or a control antibody C-MAb at 4° C. for 30 minutes, washed in DME/Hepes, and then exposed for an additional 30 minutes at 4° C. in the dark to varying concentrations of RαMIg-Hp or RαMIg-Gp between 2 μg/ml and 15 ng/ml of Hp or Gp. The cells are assessed for viability using labeled thymidine uptake as described above. These results for Ig-Hp are shown in Table 3.

TABLE 3

| RαMIg-Hp | Primary antibody | |
|---|---|---|
| (ng/ml) | B16G | C—MAb |
| 500 | 100 | 30 |
| 250 | 85 | 22 |
| 125 | 75 | 5 |
| 52.5 | 60 | 2 |
| 31.2 | 47 | 3 |
| 15.6 | 18 | 1.5 |

Similar results are obtained using corresponding conjugates with Gp.

EXAMPLE 5

In Vivo Cytotoxicity of the Immunoconjugates

The efficacy of the conjugates and of the Gp compounds of the invention in vivo is also assessed. For the CAMAL-1 and anti-M1 conjugates, the procedures are as described in the two Mew, et al, papers referenced above in Example 4. The Gp compound alone shows superior results at appropriate wavelengths as compared to the Hp labeled conjugates.

For the B16G-Hp or B16G-Gp conjugates and for the Gp (formula 1) alone, the in vivo studies are conducted as follows:

The in vivo test relies on the indirect effect of a population of T-suppressor cells on tumors, which then serve as means to assess the effectiveness of the irradiation treatment. P815 mastocytoma cells grown in syngeneic DBA/2 mice stimulate T-suppressor cells specific for the tumor. These T-suppressor cells impede the development of specific T-killer cells which would otherwise aid in the regression of the tumor. The T-cell hybridoma designated A10 above secretes a T-suppressor factor which is associated with these T-suppressor cells. Thus, selective killing of these T-suppressor cell populations through reaction with conjugates in which the Ig is an antibody specific for the T-suppressor factor on the surface of the cells (namely B16G) should result in tumor regression in mice bearing the P815 tumors.

Therefore, in this assay, DBA/2 mice are injected in the right flank subcutaneously with $10^4$ P815 cells to incorporate the tumor. On day eight, when the tumors are palpable (approx. 25-42 sq mm) the mice are randomly sorted into groups of eight and injected IV with 150 μl PBS containing nothing, Hp or Gp, B16G-Hp or B16G-Gp, B16G plus either drug, B16G alone or C-MAb-Hp or C-MAb-Gp. The levels of Hp are 50 μg per animal in all cases and B16G 310 μg in all cases (where appropriate).

The animals are maintained in the dark for two hours and then exposed to strong light at 300-750 nm and 22.5 mW/cm$^2$. The animals were then treated normally and monitored on a daily basis.

Animals treated with B16G Hp survived and were tumor free after 100 days. Results obtained are shown in Table 4.

TABLE 4

| Experiment | Treatment | Mean survival time (days) | No. of cures | % tumor-free after 100 days |
|---|---|---|---|---|
| 1 | PBS | 25.0 | 0/7 | 0 |
|  | B16G-HP | 41.3 | 3/9 | 33 |
| 2 | PBS | 23.5 | 0/6 | 0 |
|  | Hp | 21.0 | 0/8 | 0 |
|  | B16G-Hp | 24.2 | 3/8 | 37.5 |
| 3 | PBS | 24.1 | 0/7 | 0 |
|  | Hp | 23.4 | 0/7 | 0 |
|  | B16G + HP | 23.5 | 0/6 | 0 |
|  | B16G-Hp | 29.2 | 2/7 | 29 |
| 4 | PBS | 25.2 | 0/8 | 0 |
|  | B16G | 28.3 | 0/8 | 0 |
|  | Hp | 24.2 | 0/8 | 0 |
|  | B16G + Hp | 24.6 | 0/7 | 0 |
|  | B16G-Hp | 36.7 | 3/7 | 43 |
| 5 | PBS | 23.8 | 0/8 | 0 |
|  | Hp | 27.0 | 0/8 | 0 |
|  | C—MAb-Hp | 20.3 | 0/8 | 0 |
|  | B16G-HP | 34.0 | 1/8 | 12.5 |

Similar results are obtained for Gp alone or Gp conjugates.

We claim:

1. A method to impair the functioning of target cells to which a hydro-monobenzoporphyrin (Gp) having a light absorption maximum between 670-720 nm is attracted, which method comprises administering to a mammal in need of such treatment an effective amount of said Gp; and irradiating said target cells with radiation having a wavelength contained in the range of 670-720 nm, wherein the Gp is selected from the group consisting of

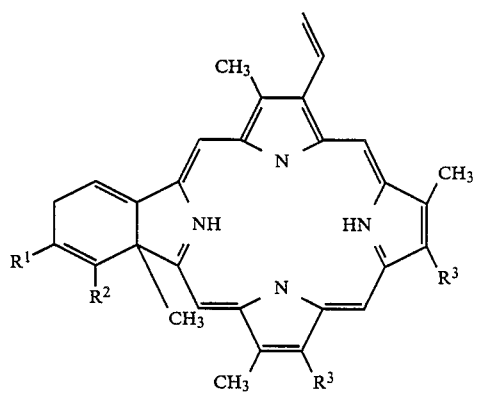

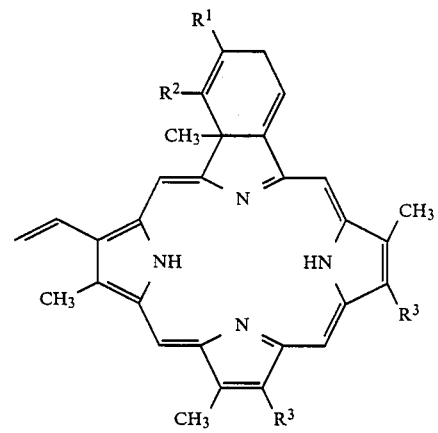

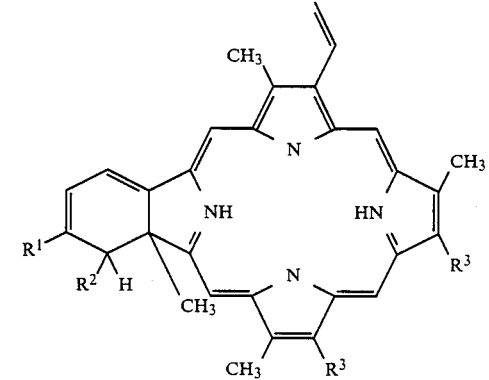

-continued

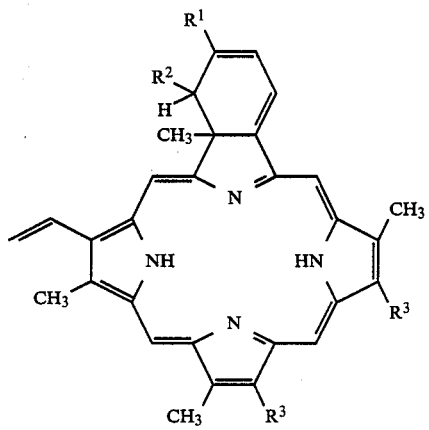

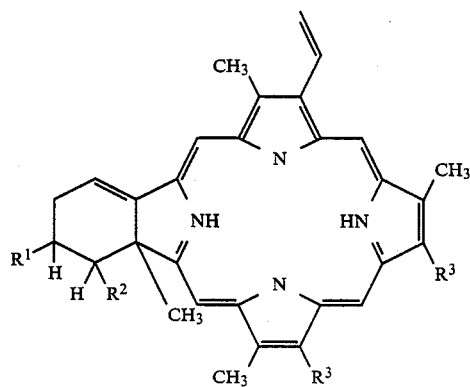

and

-continued

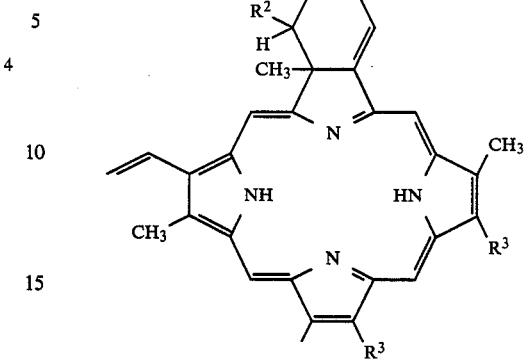

wherein each $R^3$ is independently [2-carboxyethyl or a derivative thereof] lower alkyl (1–4C) or omegacarboxyalkyl (2–6C) or the esters (1–6C) or amides (1–10C) thereof; and each $R^1$ and $R^2$ is independently selected from the group consisting of carboxy, carbalkoxy (1–6C), alkyl (1–6C) sulfone, and aryl.

2. The method of claim 1 wherein each $R^1$ and $R^2$ is independently selected from the group consisting of carboxy and carbalkoxy (1–6C).

3. The method of claim 2 wherein each $R^3$ is independently selected from the group consisting of omegacarboxyalkyl (2–6C) and the esters (1–6C) thereof.

4. The method of claim 3 wherein the Gp has the formula selected from formulas 1 and 2.

5. The method of claim 3 wherein the Gp has the formula selected from formulas 5 and 4.

6. The method of claim 3 wherein the Gp has the formula selected from formulas 5 and 6.

7. The method of claim 1 wherein $R^1$ and/or $R^2$ is conjugated to a linker-moiety.

8. The method of claim 1 wherein each $R^3$ is independently selected from the group consisting of omegacarboxyalkyl (2–6C) and the esters (1–6C) thereof.

9. The method of claim 1 wherein the target cells are present on the skin.

10. The method of claim 9 wherein the target cells are superficial tumors.

11. The method of claim 9 wherein each $R^1$ and $R^2$ is selected from the group consisting of carboxy, carbalkoxy(1–6C), alkyl(1–6C) sulfonate, alkyl(1–6C) sulfone, and aryl, optionally conjugated to a linker moiety.

* * * * *

UNITED STATES PATENT AND TRADEMARK OFFICE
CERTIFICATE OF CORRECTION

PATENT NO. : 4,883,790
APPLICATION NO. : 07/041680
DATED : November 28, 1989
INVENTOR(S) : Levy et al.

It is certified that error appears in the above-identified patent and that said Letters Patent is hereby corrected as shown below:

The drawing sheet, consisting of Fig. 1, Fig. 1-3, Fig. 5 and Fig. 6, should be deleted to be replaced with drawing sheet, consisting of Fig. 1, Fig. 1-3, Fig. 5 and Fig. 6 as shown on the attached page.

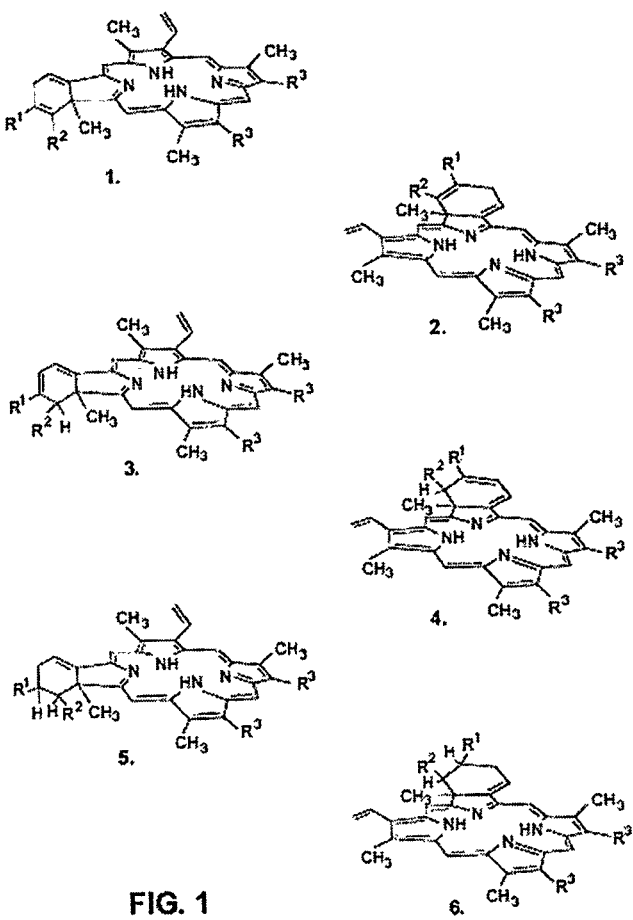

FIG. 1

UNITED STATES PATENT AND TRADEMARK OFFICE
CERTIFICATE OF CORRECTION

PATENT NO. : 4,883,790  
APPLICATION NO. : 07/041680  
DATED : November 28, 1989  
INVENTOR(S) : Levy et al.

It is certified that error appears in the above-identified patent and that said Letters Patent is hereby corrected as shown below:

Replacement Drawing, Claim 1, Compound 1, Column 12, Lines 18-33

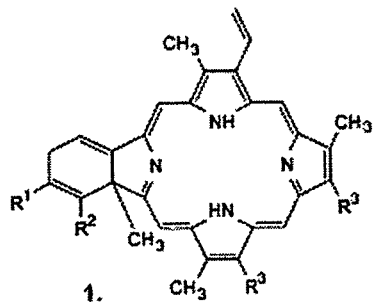

Replacement Drawing, Claim 1, Compound 3, Column 12, Lines 53-67

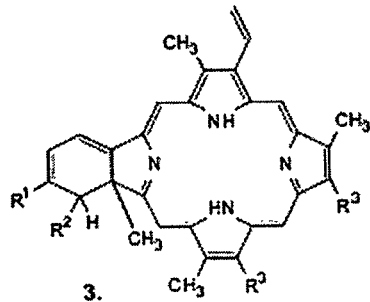

Replacement Drawings, Claim 1, Compound 5, Column 13, Lines 28-43

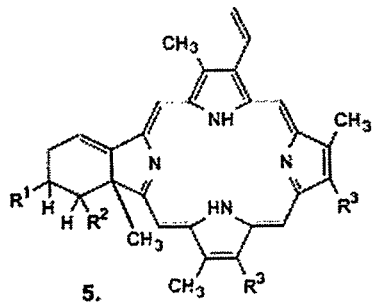

UNITED STATES PATENT AND TRADEMARK OFFICE
CERTIFICATE OF CORRECTION

PATENT NO. : 4,883,790
APPLICATION NO. : 07/041680
DATED : November 28, 1989
INVENTOR(S) : Levy et al.

It is certified that error appears in the above-identified patent and that said Letters Patent is hereby corrected as shown below:

Replacement Drawing, Claim 1, Compound 6, Column 14, Lines 2-19

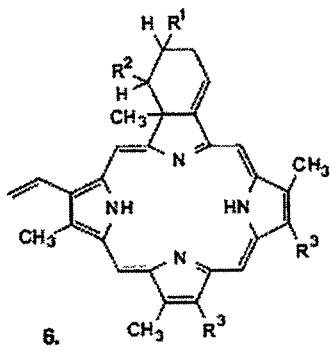

Signed and Sealed this

Twenty-fourth Day of October, 2006

JON W. DUDAS
*Director of the United States Patent and Trademark Office*